(12) United States Patent
Halverson et al.

(10) Patent No.: US 10,975,220 B2
(45) Date of Patent: Apr. 13, 2021

(54) ARTICLES INCLUDING A POROUS ELASTOMERIC MATERIAL WITH AN INTEGRATED ELASTOMERIC MATERIAL AND METHODS OF MAKING SAME

(71) Applicant: 3M INNOVATIVE PROPERTIES COMPANY, St. Paul, MN (US)

(72) Inventors: Kurt J. Halverson, Lake Elmo, MN (US); Cary A. Kipke, Austin, TX (US)

(73) Assignee: 3M Innovative Properties Company, St. Paul, MN (US)

(*) Notice: Subject to any disclaimer, the term of this patent is extended or adjusted under 35 U.S.C. 154(b) by 65 days.

(21) Appl. No.: 15/309,596

(22) PCT Filed: May 6, 2015

(86) PCT No.: PCT/US2015/029345
§ 371 (c)(1),
(2) Date: Nov. 8, 2016

(87) PCT Pub. No.: WO2015/175270
PCT Pub. Date: Nov. 19, 2015

(65) Prior Publication Data
US 2017/0182202 A1    Jun. 29, 2017

Related U.S. Application Data

(60) Provisional application No. 61/994,465, filed on May 16, 2014.

(51) Int. Cl.
*C08J 9/36* (2006.01)
*A61F 13/00* (2006.01)
(Continued)

(52) U.S. Cl.
CPC ......... *C08J 9/365* (2013.01); *A61F 13/00068* (2013.01); *A61F 13/0216* (2013.01);
(Continued)

(58) Field of Classification Search
CPC .............................. C08J 9/365; C08J 2205/05
See application file for complete search history.

(56) References Cited

U.S. PATENT DOCUMENTS 2,955,056 A   10/1960   Knox
5,720,915 A   2/1998   Joppen
(Continued)

FOREIGN PATENT DOCUMENTS

DE   3622906   1/1988
EP   0012849   7/1980
(Continued)

OTHER PUBLICATIONS

International Search Report for PCT International Application No. PCT/US2015/029345, dated Aug. 17, 2015, 4 pages.

*Primary Examiner* — Hai Vo
(74) *Attorney, Agent, or Firm* — Qiang Han

(57) ABSTRACT

Articles are provided, including a porous elastomeric material having a first major surface and an elastomeric material integrated into the first major surface of the porous elastomeric material. The elastomeric material coating the first major surface, a first portion of the elastomeric material being disposed within a plurality of pores defined by the first major surface of the porous elastomeric material and extending into the plurality of pores to a depth of at least 300 micrometers (μm), wherein the first portion of the elastomeric material provides fluid communication through the porous elastomeric material via holes formed in the elastomeric material extending into the thickness of the porous elastomeric material through the voids of the pores of the elastomeric material. A method of making an article is also provided.

16 Claims, 6 Drawing Sheets

(51) Int. Cl.
    *A61L 15/42*     (2006.01)
    *A61F 13/02*     (2006.01)
    *A61M 1/00*     (2006.01)
    *A61L 15/26*     (2006.01)

(52) U.S. Cl.
CPC ............ *A61L 15/26* (2013.01); *A61L 15/425* (2013.01); *A61M 1/0088* (2013.01); *C08J 2205/05* (2013.01); *C08J 2300/22* (2013.01); *C08J 2300/26* (2013.01); *C08J 2375/04* (2013.01); *C08J 2400/22* (2013.01); *C08J 2400/26* (2013.01); *C08J 2429/04* (2013.01); *C08J 2475/04* (2013.01); *Y10T 428/249955* (2015.04); *Y10T 428/249958* (2015.04); *Y10T 428/249991* (2015.04)

(56) References Cited

U.S. PATENT DOCUMENTS

| | | | |
|---|---|---|---|
| 6,821,366 B2 | 11/2004 | Allison | |
| 7,097,723 B2 | 8/2006 | Allison | |
| 7,105,069 B2 | 9/2006 | Allison | |
| 7,700,176 B2 | 4/2010 | Allison | |
| 7,700,819 B2 | 4/2010 | Ambrosio | |
| 7,758,554 B2 | 7/2010 | Lina | |
| 2003/0099810 A1 | 5/2003 | Allison | |
| 2004/0234685 A1 | 11/2004 | Allison | |
| 2005/0051264 A1 | 3/2005 | Allison | |
| 2005/0064779 A1 | 3/2005 | Allison | |
| 2008/0274307 A1 | 11/2008 | Chereau | |
| 2009/0270820 A1 | 10/2009 | Johnson | |
| 2010/0256777 A1* | 10/2010 | Datta | A61L 27/18 623/23.72 |
| 2011/0015595 A1 | 1/2011 | Robinson | |
| 2011/0251566 A1 | 10/2011 | Zimnitsky | |
| 2012/0276339 A1 | 11/2012 | Pearce | |
| 2012/0325403 A1 | 12/2012 | Chereau | |

FOREIGN PATENT DOCUMENTS

| | | |
|---|---|---|
| EP | 0718077 | 6/1996 |
| GB | 1519795 | 8/1978 |
| JP | 2010-023504 A | 2/2010 |
| WO | WO 2002-066244 | 8/2002 |
| WO | WO 2009-089016 | 7/2009 |
| WO | WO 2012-082716 | 6/2012 |

\* cited by examiner

ARTICLES INCLUDING A POROUS ELASTOMERIC MATERIAL WITH AN INTEGRATED ELASTOMERIC MATERIAL AND METHODS OF MAKING SAME

FIELD

Articles are provided including a porous elastomeric material having an elastomeric material integrated with the porous elastomeric material, and methods of making the articles are provided.

BACKGROUND

Negative pressure wound therapy (NPWT) has been clinically demonstrated to enhance wound healing. The therapy comprises applying a dressing layer on the wound site, covering the dressing with a thin elastomeric drape that extends over the dressing to the periwound skin, and creating a hole or via in the drape to which a vacuum source is coupled. Vacuum is applied to the system, which serves to both conformally compress the dressing against the tissue and remove wound exudate. A variety of dressing materials have been utilized, however it has been demonstrated that reticulated, open cell foam provides an advantageous healing response.

The use of open cell foam for this therapy has numerous advantages. First, when compressed foam conforms uniformly to the tissue and voids between the dressing and the wound bed are minimized Second, the open cell structure provides a continuous pathway for exudate removal throughout the entire wound bed. Third, vacuum is evenly distributed through the pores, minimizing pressure drop as a function of distance from the vacuum port. Finally, the foam typically used for NPWT compresses approximately 50% at therapeutic vacuum levels (~150 mm Hg). This change in volume decreases the overall size of the wound.

One significant disadvantage of open cell foam is "ingrowth" of new tissue into the pores of the open cell foam. As treatment progresses the newly formed tissue extends into the pores, eventually surrounding and encapsulating a portion of the foam inside the new tissue. Once embedded, removal of the foam becomes problematic. It is traumatic to the patient, often requiring sedation to alleviate the pain. If the foam is stronger than the tissue, it pulls the new tissue apart during removal causing damage and bleeding. If the new tissue is stronger than the foam, sections of foam break off and remain embedded in the tissue causing inflammation and irritation. To mitigate ingrowth, contact layers placed between the foam and the tissue have been utilized, including gauze, nonwovens, perforated films and microstructured films, however diminished healing response is frequently observed using these approaches.

Hence, there remains a need for an article that retains the benefits of foam while also minimizing or preventing tissue ingrowth.

SUMMARY

Articles are provided including a porous elastomeric material with an integrated elastomeric material. In a first aspect, an article is provided. More particularly, an article is provided including a porous elastomeric material having a first major surface and an elastomeric material integrated into the first major surface of the porous elastomeric material. The elastomeric material coating the first major surface, a first portion of the elastomeric material being disposed within a plurality of pores defined by the first major surface of the porous elastomeric material and extending into the plurality of pores to a depth of at least 300 micrometers (μm), wherein the first portion of the elastomeric material provides fluid communication through the porous elastomeric material through the elastomeric material and holes formed therein and extending into the thickness of the porous elastomeric material through the voids of the pores.

In a second aspect, a method of making an article is provided. The method includes providing a porous elastomeric material having a first major surface, providing an elastomeric material, contacting the elastomeric material with the first major surface of the porous elastomeric material, and applying force to the elastomeric material thereby coating the first major surface and drawing a first portion of the elastomeric material into a plurality of pores defined by the first major surface of the porous elastomeric material and extending into the plurality of pores to a depth of at least 300 μm. The first portion of the elastomeric material provides communication into the porous elastomeric material through the elastomeric material extending into the thickness of the porous elastomeric material through the voids of the pores.

Use of the articles, for example in negative pressure wound therapy, minimizes tissue ingrowth because as tissue grows, the elastomeric material extending into the plurality of pores physically blocks encapsulation of the porous elastomeric material by the new tissue growth. In addition, the wound dressing material also supports exudate removal via macroscopic pores through the elastomeric material.

Figure 1:
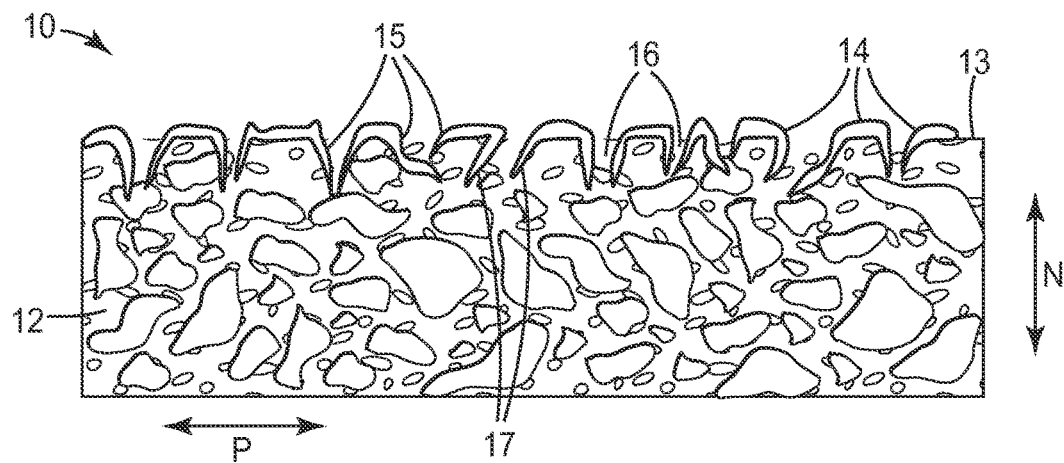
FIG. 1 is an exemplary cross-sectional schematic of an article including an elastomeric material integrated into the first major surface of a porous elastomeric material.

While the above-identified drawings, which may not be drawn to scale, set forth various embodiments of the present disclosure, other embodiments are also contemplated, as noted in the Detailed Description.

DETAILED DESCRIPTION

Articles including a porous elastomeric material having an elastomeric material integrated with the porous elastomeric material and methods of making the articles are provided. More specifically, the article has a porous elastomeric material having a first major surface and an elastomeric material integrated into the first major surface of the porous elastomeric material.

The recitation of any numerical range by endpoints is meant to include the endpoints of the range, all numbers within the range, and any narrower range within the stated range (e.g. 1 to 5 includes 1, 1.5, 2, 2.75, 3, 3.8, 4, and 5). Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

For the following Glossary of defined terms, these definitions shall be applied for the entire application, unless a different definition is provided in the claims or elsewhere in the specification.

Glossary

Certain terms are used throughout the description and the claims that, while for the most part are well known, may require some explanation. It should be understood that, as used herein:

The term "a", "an", and "the" are used interchangeably with "at least one" to mean one or more of the elements being described.

The term "and/or" means either or both. For example, the expression "A and/or B" means A, B, or a combination of A and B.

The term "polymeric material" refers to a substance composed of at least one polymer.

The term "elastomeric" refers to any material that is able to resume its original shape when a deforming force is removed.

The term "latex" refers to a water emulsion of a synthetic polymer.

The term "porous" refers to any material containing voids.

The term "foam" refers to an open cell polymeric material.

The term "communication" refers to passage between more than one location. For example, a material could traverse from a first area to a second area that is in communication with the first area.

In a first aspect, an article is provided. More particularly, an article is provided comprising a porous elastomeric material comprising a first major surface; and an elastomeric material integrated into the first major surface of the porous elastomeric material, the elastomeric material coating the first major surface, a first portion of the elastomeric material being disposed within a plurality of pores defined by the first major surface of the porous elastomeric material and extending into the plurality of pores to a depth of at least 300 micrometers (μm), wherein the first portion of the elastomeric material provides communication into the porous elastomeric material through the elastomeric material extending into the thickness of the porous elastomeric material through the voids of the pores.

Referring to FIG. 1, an exemplary cross-sectional schematic is provided of one such article. The article 10 comprises a porous elastomeric material 12 having a first major surface 13 and an elastomeric material 14 integrated into the first major surface 13 of the porous elastomeric material 12. The elastomeric material 14 coats the first major surface 13, with a first portion of the elastomeric material 15 being disposed within a plurality of pores 16 defined by the first major surface 13 of the porous elastomeric material 12 and extending into the plurality of pores 16 to a depth of at least 300 μm. The first portion of the elastomeric material 15 provides communication into the porous elastomeric material 12 through the elastomeric material 14 extending into the thickness of the porous elastomeric material 12 through the voids of the pores 16. Typically, the first portion of the elastomeric material 15 comprises a wall thickness 17 that decreases as the depth into the porous elastomeric material increases. The decreasing wall thickness 17 generally occurs as a result of the elastomeric material 14 being stretched into the pores 16 to form the first portion of the elastomeric material 15. The term "the first portion of the elastomeric material" refers collectively to the plurality of individual sections of the elastomeric material that is disposed within the pores defined by the first major surface of the porous elastomeric material and extends into the plurality of pores, providing communication into the porous elastomeric material through the voids of the pores.

In certain embodiments, the article has a thickness of at least 5 millimeters (mm), at least 10 mm, at least 15 mm, at least 20 mm, at least 25 mm, or even at least 30 mm, and a thickness of up to 50 mm, or up to 45 mm, or up to 40 mm, or up to 35 mm. In an embodiment, the article has a thickness of 5 mm to 50 mm.

Depending on the use of the article, a suitable depth to which the elastomeric material disposed within the plurality of pores extends is selected. In certain embodiments, the first portion of the elastomeric material extends to a depth of at least 300 μm, at least 400 μm, at least 500 μm, or even at least 600 μm, into the plurality of pores of the porous elastomeric material. In certain embodiments, the first portion of the elastomeric material extends to a depth of up to 500 µm, up to 600 µm, up to 800 µm, 1000 µm, up to 1100 µm, or even up to 1200 µm, into the plurality of pores of the porous elastomeric material. Preferably, the first portion of the elastomeric material disposed within the plurality of pores extends to a depth of between 300 µm and 1000 µm.

The first portion of the elastomeric material 15 disposed within the plurality of pores 16 blocks communication through the porous elastomeric material 12 in a direction P parallel to the first major surface 13. Advantageously, blockage of the pores in a direction parallel to the first major surface prevents tissue growth from encapsulating the porous elastomeric material during NPWT, thereby minimizing undesirable tissue ingrowth. In certain embodiments, communication through the porous elastomeric material in a direction parallel to the first major surface is blocked between a depth of 50 µm and 1000 µm into the porous elastomeric material. For effective use during NPWT, pore passageways are isolated from each other such that no two adjacent pores join and/or that there is no conduit between adjacent passageways. Hence, tissue growth is prevented from encapsulating porous elastomeric material by blocking communication through the porous elastomeric material, such as blocking communication through the porous elastomeric material in a direction generally parallel to the first major surface.

The surface roughness of the porous elastomeric material will dictate the initial depth from which communication is blocked in a direction parallel to the first major surface, as an uneven coated surface is not capable of effectively blocking communication at the location of the first major surface. If the porous elastomeric material has a surface roughness of 100 µm at the first major surface, for example, communication can be blocked by the first portion of elastomeric material starting at about 100 µm into the thickness of the porous elastomeric material. If the article is compressed during use such that the surface roughness is condensed; however, communication may be blocked starting at the first major surface of the porous elastomeric material. The maximum depth to which communication is blocked may be selected depending on the intended use of the article. In an aspect, the depth is selected with respect to an amount of tissue growth expected during use of an article in NPWT. For instance, if an exemplary article will be in use for NPWT for a time of five days and the wound tissue is capable of growing about 100 µm per day, a suitable depth to which communication is blocked would be greater than 500 µm to prevent tissue encapsulation of any of the porous elastomeric material.

Figure 2:
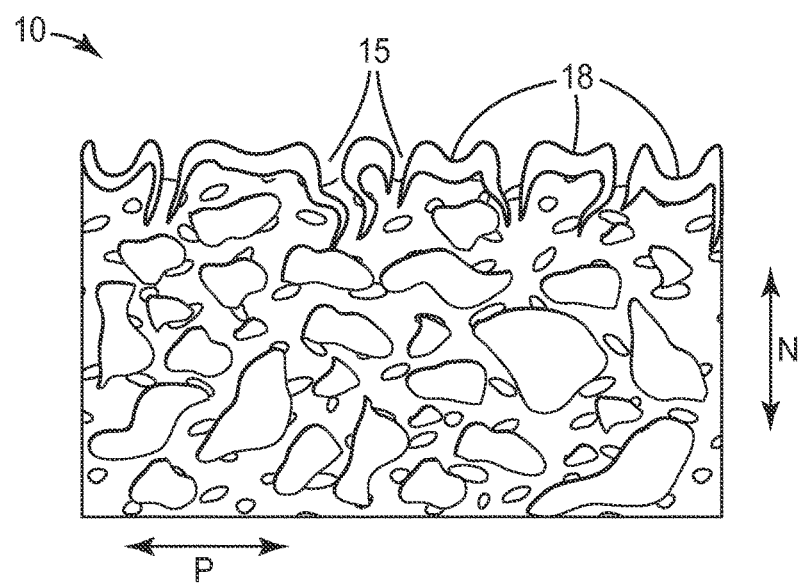
FIG. 2 is another exemplary cross-sectional schematic of an article including an elastomeric material integrated into the first major surface of a porous elastomeric material.

Referring to FIG. 2, in many embodiments the article 10 further includes a second portion of the elastomeric material 18 being disposed within a plurality of pores 16 defined by the first major surface 13 of the porous elastomeric material 12 and extending into the plurality of pores to an average depth of less than 300 µm. The term "the second portion of the elastomeric material" refers collectively to the plurality of individual sections of the elastomeric material that is disposed within a plurality of pores defined by the first major surface of the porous elastomeric material, extending into the plurality of pores, which blocks communication into the porous elastomeric material in a direction normal to the first major surface. The second portion of the elastomeric material 18 blocks communication into the porous elastomeric material 12 in a direction N normal to the first major surface 13. The second portion of the elastomeric material 18 is typically formed when force is applied to the elastomeric material that is insufficient to form a hole in the elastomeric material at the location of a pore in the porous elastomeric material. The amount (i.e., surface area) of the coated first major surface that is coated by the second portion of the elastomeric material is typically between 10% and 80%, such as between 15% and 55% of the first major surface. When used for NPWT, an article preferably has enough pores defined by the first major surface open for an even application of the negative pressure and for effective exudate removal, such as at least 20%, at least 30%, at least 40%, at least 50%, or at least 60% of the pores being open at the first major surface.

Figure 3:
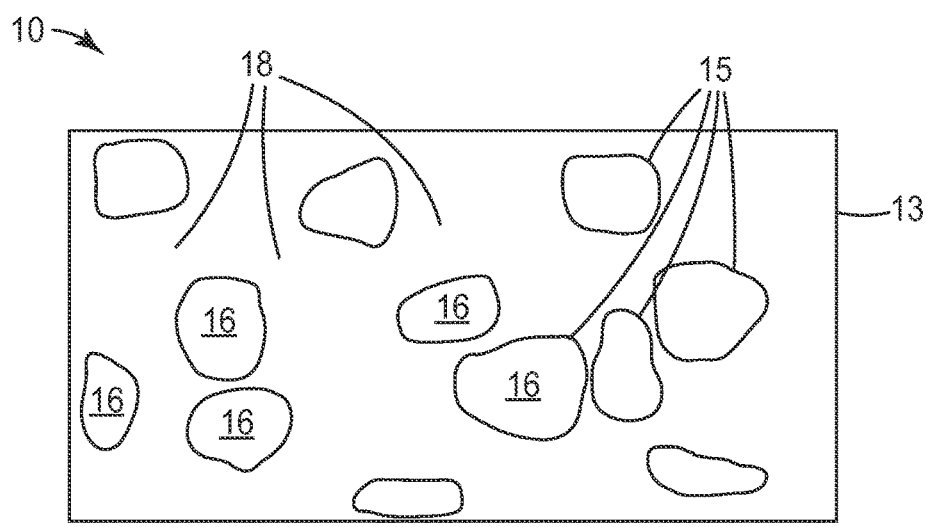
FIG. 3 is a top view schematic of an exemplary article including an elastomeric material integrated into the first major surface of a porous elastomeric material.

Referring to FIG. 3, a top view schematic of an article 10 is provided showing first major surface 13 of the porous elastomeric material 12 including the first portion of elastomeric material 15 extending into the plurality of pores 16 and the second portion of elastomeric material 18 blocking communication into the porous elastomeric material 12 in the direction N normal to the first major surface 13. FIG. 3 further illustrates that the sections of the first portion of the elastomeric material and of the second portion of the elastomeric material are interspersed amongst each other on the first major surface of the porous elastomeric material. Preferably, the entire first major surface of the porous elastomeric material is coated by a combination of the first portion and the second portion of the elastomeric material. In certain aspects, however, less than 100% of the first major surface is coated by the elastomeric material, such as at least 50%, at least 60%, at least 70%, at least 80%, at least 90%, or even at least 95% of the first major surface of the porous elastomeric material is coated by a combination of the first portion and the second portion of the elastomeric material.

Figure 4:
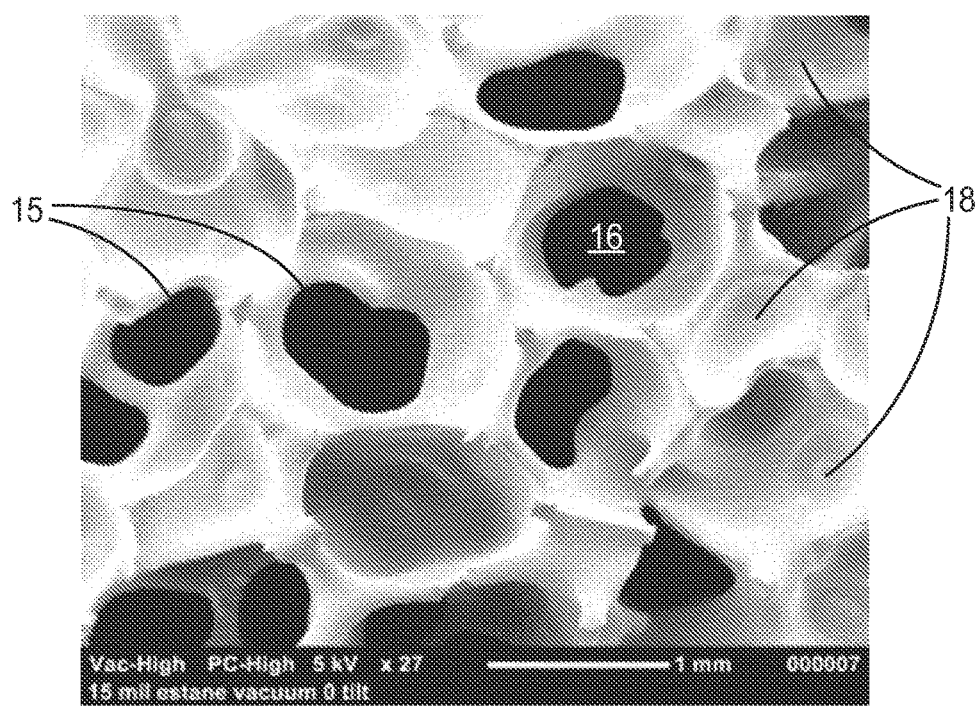
FIG. 4 is a Scanning Electron Microscopy (SEM) image of an exemplary article including an elastomeric material integrated into the first major surface of a porous elastomeric material.

Similar to FIG. 3, FIG. 4 is a Scanning Electron Microscopy (SEM) image of an exemplary article including an elastomeric material integrated into the first major surface of a porous elastomeric material. FIG. 4 shows a first major surface of a porous elastomeric material including both a first portion of elastomeric material 15 extending into the plurality of pores 16 and a second portion of elastomeric material 18 blocking pores into the porous elastomeric material.

Typically, the porous elastomeric material comprises an average pore size of 400 µm to 700 µm, such as an average pore size of 400 µm to 600 µm. The presence of the elastomeric material integrated into the first major surface of the porous elastomeric material decreases the effective pore size of the article. In many embodiments, the first portion of the elastomeric material comprises an average pore size of 300 µm to 700 µm or 350 µm to 600 µm.

In certain embodiments, the porous elastomeric material comprises a foam, such as a sponge (natural or synthetic), a cushion, or insulation. Suitable foams include for example and without limitation, a polymeric foam comprising a polyolefin, a polyurethane, a poly(meth)acrylate, or neoprene. Synthetic foams are particularly well suited for the porous elastomeric material because the foam is a flexible, compliant material that can absorb liquid. Synthetic foams are typically less hydrophilic and have a low ability to retain liquid within the structure as compared to natural foams, such as a cellulose sponge. Therefore, although fluid is easily absorbed in the material, the fluid is also easily flushed from the less hydrophilic foam, which would be useful in drawing out exudate through the porous elastomeric material. In many embodiments, the porous elastomeric material comprises an open cell foam. One suitable foam is a polyurethane open cell foam commercially available under trade designation Crest Foam Industries, Inc. (Moonachie, N.J.).

In certain embodiments, the elastomeric material comprises latex. An advantage of employing a water emulsion of a synthetic polymer is that it can be conveniently applied to the first major surface of the porous elastomeric material using methods such as spraying, casting, dipping, etc., as known to the skilled practitioner. In alternate embodiments, the elastomeric material comprises a film that is heated past its glass transition point then drawn into the foam using vacuum. The elastomeric material typically comprises polyurethane, poly(vinyl alcohol), or a polyurethane copolymer.

The term "polyurethane" as used herein applies to polymers made from the reaction product of a compound containing at least two isocyanate groups (—N=C=O), referred to herein as "isocyanates", and a compound containing at least two active-hydrogen containing groups. Examples of active-hydrogen containing groups include primary alcohols, secondary alcohols, phenols and water. Other active-hydrogen containing groups include primary and secondary amines which react with the isocyanate to form a urea linkage, thereby making a polyurea. A wide variety of isocyanate-terminated materials and appropriate co-reactants are well known, and many are commercially available (see, for example, Gunter Oertel, "Polyurethane Handbook", Hanser Publishers, Munich (1985)). One suitable polyurethane is commercially available under the trade designation ESTANE 58309 from Lubrizol Advanced Materials, Inc. (Cleveland, Ohio). A polyurethane copolymer comprises a polyurethane copolymerized with a different polymer. Elastomeric olefins may also be used, for example propylene based elastomer (PBE) sold under the trade name Vistamaxx (Exon Mobile).

The term "poly(vinyl alcohol)" as used herein refers to poly(vinyl alcohol), derivatives thereof, and mixtures of poly(vinyl alcohol) and its derivatives. The degree of hydrolysis of PVA or its derivatives is from 50 to 100 percent, or 70 to 100 percent, or 85 to 100 percent. For example, the PVA can include up to 50 percent polyvinyl acetate. One suitable poly(vinyl alcohol) is commercially available under the trade designation V.A.C WhiteFoam from KCI International (San Antonio, Tex.).

In a second aspect a method is provided. More specifically, the method comprises providing a porous elastomeric material comprising a first major surface; providing an elastomeric material; contacting the elastomeric material with the first major surface of the porous elastomeric material; and applying force to the elastomeric material thereby coating the first major surface and drawing a first portion of the elastomeric material into a plurality of pores defined by the first major surface of the porous elastomeric material and extending into the plurality of pores to a depth of at least 300 µm. The first portion of the elastomeric material provides communication into the porous elastomeric material through the elastomeric material extending into the thickness of the porous elastomeric material through the voids of the pores.

Figure 5A:
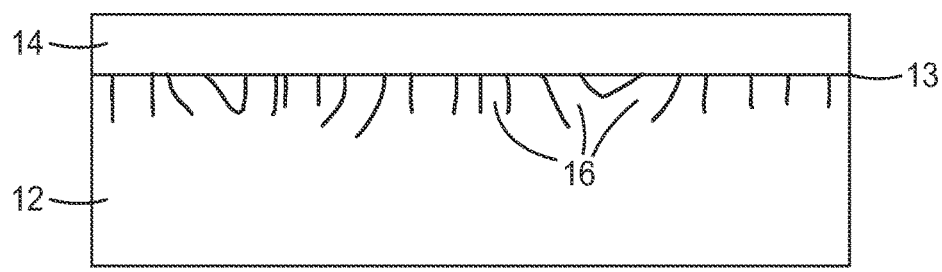
FIG. 5A is a cross-sectional schematic of making an exemplary article by contacting an elastomeric material with the first major surface of a porous elastomeric material
Figure 5B:
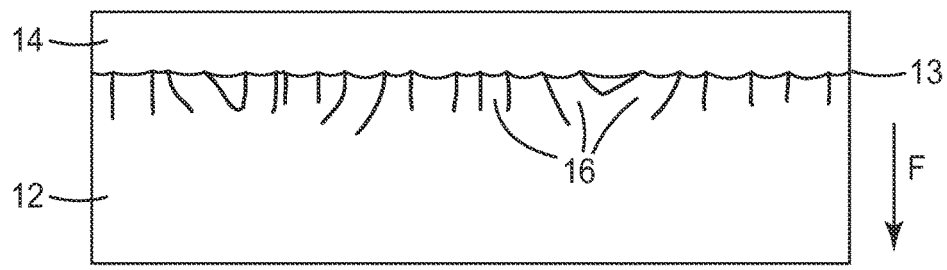
FIG. 5B is a cross-sectional schematic of making an exemplary article by applying force to the elastomeric material shown in FIG. 5A.
Figure 5C:
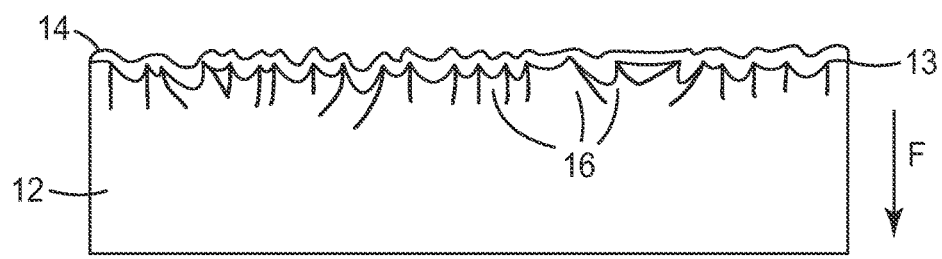
FIG. 5C is a cross-sectional schematic of making an exemplary article by continuing to apply force to the elastomeric material shown in FIG. 5B.
Figure 5D:
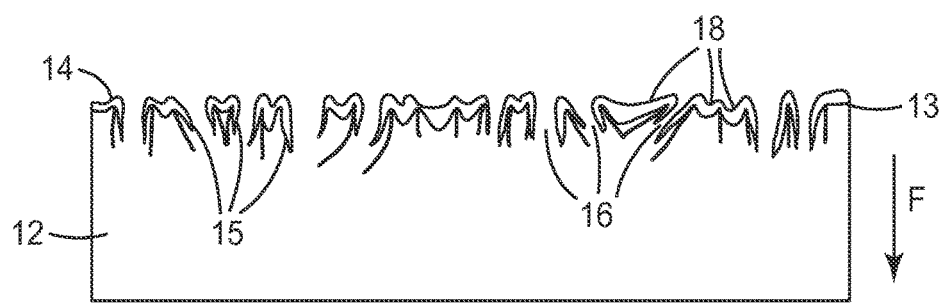
FIG. 5D is a cross-sectional schematic of an exemplary article made by continuing to apply force to the elastomeric material shown in FIG. 5C.

The method comprises providing a porous elastomeric material having a first major surface and providing an elastomeric material. Referring to FIG. 5A, in an embodiment the method further includes contacting the elastomeric material 14 with the first major surface 13 of the porous elastomeric material 12. Turning to FIGS. 5B-5D, the method also includes applying force F to the elastomeric material 14 thereby coating the first major surface 13 and drawing a first portion of the elastomeric material 15 into a plurality of pores 16 defined by the first major surface 13 of the porous elastomeric material and extending into the plurality of pores to a depth of at least 300 µm. Referring to FIG. 5D, the first portion of the elastomeric material 15 provides fluid communication through the porous elastomeric material 12 through the elastomeric material extending into the thickness of the porous elastomeric material through the voids of the pores 16 of the porous elastomeric material. FIG. 5D further illustrates a second portion of the elastomeric material 18 that blocks communication into the porous elastomeric material 12 in the direction of the thickness of the porous elastomeric material 12 (e.g., normal to the first major surface of the porous elastomeric material).

Figure 6A:
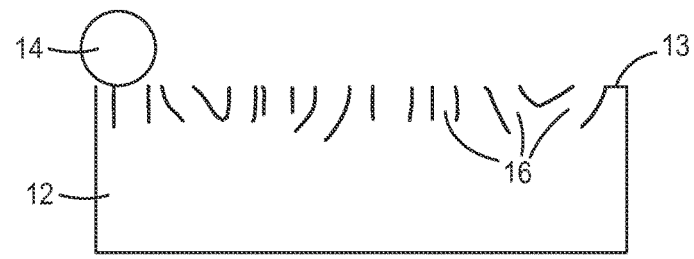
FIG. 6A is a cross-sectional schematic of making an exemplary article by contacting an elastomeric material with the first major surface of a porous elastomeric material
Figure 6B:
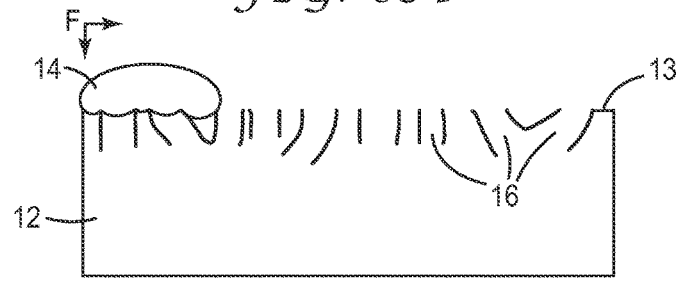
FIG. 6B is a cross-sectional schematic of making an exemplary article by applying force to the elastomeric material shown in FIG. 6A.
Figure 6C:
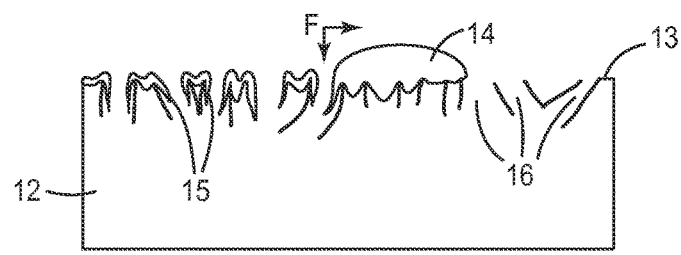
FIG. 6C is a cross-sectional schematic of making an exemplary article by continuing to apply force to the elastomeric material shown in FIG. 6B.
Figure 6D:
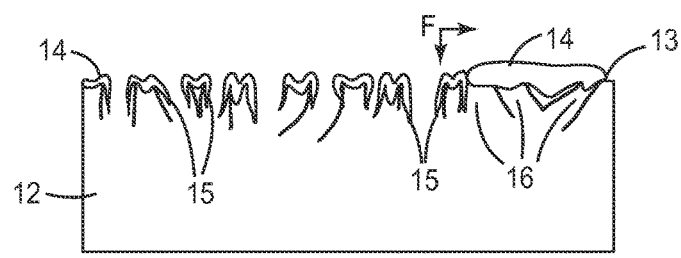
FIG. 6D is a cross-sectional schematic of making an exemplary article by continuing to apply force to the elastomeric material shown in FIG. 6C.
Figure 6E:
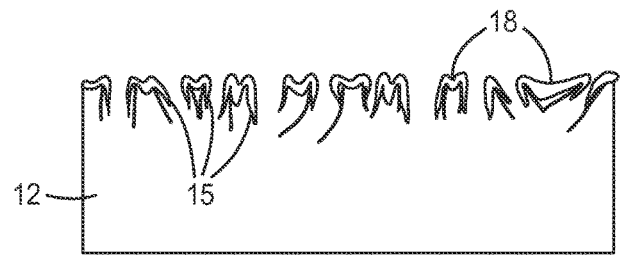
FIG. 6E is a cross-sectional schematic of an exemplary article made by continuing to apply force to the elastomeric material shown in FIG. 6D.

Referring to FIG. 6A, in an embodiment the method includes contacting the elastomeric material 14 with the first major surface 13 of the porous elastomeric material 12, such as a thick, elongated bead of elastomeric material 14. Turning to FIGS. 6B-6E, the method also includes applying force F to the elastomeric material 14 in a direction substantially parallel to the first major surface 13 of the porous elastomeric material as well as in a direction substantially normal to the first major surface 13 of the porous elastomeric material, thereby coating the first major surface 13 and drawing a first portion of the elastomeric material 15 into a plurality of pores 16 defined by the first major surface 13 of the porous elastomeric material and extending into the plurality of pores to a depth of at least 300 µm. In such an embodiment, the coating of elastomeric material 14 progresses across the area of the first major surface 13 as the force F is applied, for instance using an air knife. Referring to FIG. 6B, the force F causes the elastomeric material 14 to cover a fraction of the entire area of the first major surface, and begin impinging down into the pores 16. Referring to FIGS. 6C-6D, the force F continues to cause the elastomeric material 14 to progress across the first major surface. Moreover, the first portion of the elastomeric material 15 provides fluid communication through the porous elastomeric material 12 through the elastomeric material extending into the thickness of the porous elastomeric material through the voids of the pores 16 of the porous elastomeric material. FIG. 6E further illustrates a second portion of the elastomeric material 18 that blocks communication into the porous elastomeric material 12 in the direction of the thickness of the porous elastomeric material 12 (e.g., normal to the first major surface of the porous elastomeric material).

The force applied to the elastomeric material is not particularly limited. In certain embodiments the force is positive pressure and the elastomeric material is located between the porous elastomeric material and a source of the positive pressure. The force may be provided by a flow of gas, for example and without limitation, a flow of air, nitrogen, argon, or a combination thereof. In certain embodiments, the force is a vacuum and the porous elastomeric material is located between the elastomeric material and a source of the vacuum. Alternatively, the force is gravity or centrifugal force. Preferably, the force is evenly applied over the entire elastomeric material to maximize achievement of formation of the first portion and a consistent depth to which the first portion of the elastomeric material extends into the porous elastomeric material.

As mentioned above, the elastomeric material is optionally provided as a film or a latex. In an aspect, the step of providing the elastomeric material comprises providing a film having a thickness of at least 5 µm, at least 7 µm, at least 9 µm, at least 11 µm, at least 13 µm, or even at least 15 m, and a thickness of up to 20 µm, up to 18 µm, up to 16 µm, up to 14 µm, up to 12 µm, or even up to 10 µm. Hence, the film typically has a thickness between 5 µm and 20 µm. In certain embodiments, the step of providing the elastomeric material includes providing a melted film, and the contacting the elastomeric material includes casting the melted film on the first major surface of the porous elastomeric material. An advantage of providing a melted film is that less force will be required to draw the elastomeric material into the pores of the porous elastomeric material than a film that has not been heated.

Alternatively, the step of providing the elastomeric material may comprise providing a water-soluble emulsion containing a solvent and an elastomeric material dispersed in the solvent or providing a solution comprising an elastomeric material dissolved in an organic solvent. Contacting the elastomeric material with a water-soluble emulsion or solution is not particularly limited, and usually includes casting, coating, or spraying the water-soluble emulsion or the solution on the first major surface of the porous elastomeric material. When employing an emulsion or solution, the method further generally includes evaporating at least some of the solvent after contacting the elastomeric material with the first major surface of the porous elastomeric material.

The article made by the method is as described in detail above with respect to the first aspect.

Various items are described that are articles or methods of making articles.

Embodiment 1 is an article including a porous elastomeric material having a first major surface and an elastomeric material integrated into the first major surface of the porous elastomeric material. The elastomeric material coats the first major surface, and a first portion of the elastomeric material is disposed within a plurality of pores defined by the first major surface of the porous elastomeric material and extending into the plurality of pores to a depth of at least 300 micrometers ($\mu$m). The first portion of the elastomeric material provides fluid communication through the porous elastomeric material via holes formed in the elastomeric material extending into the thickness of the porous elastomeric material through the voids of the pores of the porous elastomeric material.

Embodiment 2 is an article of embodiment 1, wherein the first portion of the elastomeric material disposed within the plurality of pores extends to a depth of between 300 $\mu$m and 1000 $\mu$m.

Embodiment 3 is an article of embodiment 1 or embodiment 2 wherein the first portion of the elastomeric material comprises a wall thickness that decreases as the depth into the porous elastomeric material increases.

Embodiment 4 is an article of any of embodiments 1 to 3 wherein the first portion of the elastomeric material disposed within the plurality of pores blocks communication through the porous elastomeric material in a direction parallel to the first major surface.

Embodiment 5 is an article of embodiment 4 wherein communication through the porous elastomeric material in a direction parallel to the first major surface is blocked between a depth of 50 $\mu$m and 1000 $\mu$m into the porous elastomeric material.

Embodiment 6 is an article of any of embodiments 1 to 5 further comprising a second portion of the elastomeric material being disposed within a plurality of pores defined by the first major surface of the porous elastomeric material and extending into the plurality of pores to an average depth of less than 300 $\mu$m, wherein the second portion of the elastomeric material blocks communication into the porous elastomeric material in a direction normal to the first major surface.

Embodiment 7 is an article of embodiment 6 wherein between 10% and 70% of the first major surface is coated by the second portion of the elastomeric material.

Embodiment 8 is an article of embodiment 6 or embodiment 7 wherein between 15% and 55% of the first major surface is coated by the second portion of the elastomeric material.

Embodiment 9 is an article of any of embodiments 1 to 8 wherein the porous elastomeric material comprises an average pore size of 400 $\mu$m to 700 $\mu$m.

Embodiment 10 is an article of any of embodiments 1 to 9 wherein the porous elastomeric material comprises an average pore size of 400 $\mu$m to 600 $\mu$m.

Embodiment 11 is an article of any of embodiments 1 to 10 wherein the first portion of the elastomeric material comprises an average pore size of 300 $\mu$m to 700 $\mu$m.

Embodiment 12 is an article of any of embodiments 1 to 11 wherein the first portion of the elastomeric material comprises an average pore size of 350 $\mu$m to 600 $\mu$m.

Embodiment 13 is an article of any of embodiments 1 to 12 wherein the porous elastomeric material comprises an open cell foam.

Embodiment 14 is an article of any of embodiments 1 to 13 wherein the porous elastomeric material comprises polyurethane.

Embodiment 15 is an article of any of embodiments 1 to 14 wherein the elastomeric material comprises latex.

Embodiment 16 is an article of any of embodiments 1 to 15 wherein the elastomeric material comprises polyurethane, poly(vinyl alcohol), or a polyurethane copolymer.

Embodiment 17 is an article of any of embodiments 1 to 16 wherein the article comprises a thickness of 5 millimeters (mm) to 50 mm.

Embodiment 18 is method of making an article including providing a porous elastomeric material comprising a first major surface, providing an elastomeric material, contacting the elastomeric material with the first major surface of the porous elastomeric material, and applying force to the elastomeric material thereby coating the first major surface and drawing a first portion of the elastomeric material into a plurality of pores defined by the first major surface of the porous elastomeric material and extending into the plurality of pores to a depth of at least 300 $\mu$m. The first portion of the elastomeric material provides fluid communication through the porous elastomeric material via holes formed in the elastomeric material extending into the thickness of the porous elastomeric material through the voids of the pores of the elastomeric material.

Embodiment 19 is a method of embodiment 18 wherein the force is positive pressure and the elastomeric material is located between the porous elastomeric material and a source of the positive pressure.

Embodiment 20 is a method of embodiment 18 or embodiment 19 wherein the force is provided by a flow of gas.

Embodiment 21 is a method of any of embodiments 18 to 20 wherein the force is provided by a flow of air, nitrogen, argon, or a combination thereof.

Embodiment 22 is a method of embodiment 18 wherein the force is negative pressure and the porous elastomeric material is located between the elastomeric material and a source of the negative pressure.

Embodiment 23 is a method of embodiment 18 wherein the force is gravity. Embodiment 24 is a method of any of embodiments 18 to 23 wherein the providing the elastomeric material comprises providing a film having a thickness between 5 $\mu$m and 20 $\mu$m.

Embodiment 25 is a method of any of embodiments 18 to 24 wherein the providing the elastomeric material comprises providing a melted film, and the contacting the elastomeric material comprises casting the melted film on the first major surface of the porous elastomeric material.

Embodiment 26 is a method of any of embodiments 18 to 23 wherein the providing the elastomeric material comprises providing a water-soluble emulsion comprising a solvent and an elastomeric material dispersed in the solvent or providing a solution comprising an elastomeric material dissolved in an organic solvent.

Embodiment 27 is a method of embodiment 26 wherein the contacting the elastomeric material comprises casting, coating, or spraying the water-soluble emulsion or the solution on the first major surface of the porous elastomeric material.

Embodiment 28 is a method of embodiment 26 or embodiment 27 further comprising evaporating at least some of the solvent after contacting the elastomeric material with the first major surface of the porous elastomeric material.

Embodiment 29 is a method of any of embodiments 18 to 28 wherein the first portion of the elastomeric material is disposed within the plurality of pores to a depth of between 300 μm and 1000 μm.

Embodiment 30 is a method of any of embodiments 18 to 29 wherein the first portion of the elastomeric material comprises a wall thickness that decreases as the depth into the porous elastomeric material increases.

Embodiment 31 is a method of any of embodiments 18 to 30 wherein the first portion of the elastomeric material disposed within the plurality of pores blocks communication through the porous elastomeric material in a direction parallel to the first major surface.

Embodiment 32 is a method of embodiment 31 wherein communication through the porous elastomeric material in a direction parallel to the first major surface is blocked between a depth of 50 μm and 1000 μm into the porous elastomeric material.

Embodiment 33 is a method of any of embodiments 18 to 32 wherein the applying force to the elastomeric material further comprises drawing a second portion of the elastomeric material into a plurality of pores defined by the first major surface of the porous elastomeric material and extending into the plurality of pores to a depth of up to 300 μm, wherein the second portion of the elastomeric material blocks communication into the porous elastomeric material in a direction normal to the first major surface.

Embodiment 34 is a method of embodiment 33 wherein between 10% and 70% of the first major surface is coated by the second portion of the elastomeric material.

Embodiment 35 is a method of embodiment 33 or embodiment 34 wherein between 15% and 55% of the first major surface is coated by the second portion of the elastomeric material.

Embodiment 36 is a method of any of embodiments 18 to 35 wherein the porous elastomeric material comprises an average pore size of 400 μm to 700 μm.

Embodiment 37 is a method of any of embodiments 18 to 36 wherein the porous elastomeric material comprises an average pore size of 400 μm to 600 μm.

Embodiment 38 is a method of any of embodiments 18 to 37 wherein the first portion of the elastomeric material comprises an average pore size of 300 μm to 700 μm.

Embodiment 39 is a method of any of embodiments 18 to 38 wherein the first portion of the elastomeric material comprises an average pore size of 350 μm to 600 μm.

Embodiment 40 is a method of any of embodiments 18 to 39 wherein the porous elastomeric material comprises an open cell foam.

Embodiment 41 is a method of any of embodiments 18 to 40 wherein the porous elastomeric material comprises polyurethane.

Embodiment 42 is a method of any of embodiments 18 to 41 wherein the elastomeric material comprises latex.

Embodiment 43 is a method of any of embodiments 18 to 42 wherein the elastomeric material comprises polyurethane, poly(vinyl alcohol), or a polyurethane copolymer.

Embodiment 44 is a method of any of embodiments 18 to 43 wherein the elastomeric material comprises polyurethane.

Embodiment 45 is a method of any of embodiments 18 to 44 wherein the article comprises a thickness of 5 millimeters (mm) to 50 mm.

Embodiment 46 is a method of any of embodiments 18 to 21 or 26 to 45, wherein the force is applied parallel to the first major surface of the porous elastomeric material.

Embodiment 47 is a method of any of embodiments 18 to 45, wherein the force is applied normal to the first major surface of the porous elastomeric material.

EXAMPLES

Objects and advantages of this invention are further illustrated by the following examples, but the particular materials and amounts thereof recited in these examples, as well as other conditions and details, should not be construed to unduly limit this invention. These examples are for illustrative purposes only and are not meant to be limiting on the scope of the appended claims.

Materials

Unless otherwise noted, all parts, percentages, ratios, etc., in the examples and in the remainder of the specification are by weight. Unless otherwise noted, all chemicals were obtained from, or are available from, chemical suppliers such as Sigma-Aldrich Chemical Company, St. Louis, Mo.

Formation of Porous Polymer Layer

The filter cup was removed from a 50 milliliter sterile filter device (Nalgene). A 2.54 cm (1 inch) diameter circular section was cut from a 2.5 centimeter (1 inch) thick sheet of open cell polyurethane foam (Crest Foam Industries, Inc., Moonachie, N.J., product code BC45MXA00) having an average number of lineal pores per inch of 45 (PPI), which is equivalent to 114 pores per lineal centimeter, and a density of 20.8-25.6 Kg/cubic meter (1.3-1.6 lbs/cubic foot) using a die punch. The cylindrical foam piece was sectioned with a razor blade to produce two pieces approximately 1.3 cm (0.5 inch) tall. A section was inserted in the top of the filter device and connected to a small diaphragm vacuum pump (GAST P104). A 2.54 cm (1 inch) hole was cut on the bottom of a 7.6×10.2×7.6 cm) aluminum foil pan. The pan was inverted and placed on a laboratory hot plate having a surface temperature of 325° C. A 7.6×7.6 cm sheet of urethane polymer with a thickness of 0.53 millimeters (15 mil) (ESTANE 58309) was placed on the inverted aluminum pan for approximately 15 seconds, at which time the urethane spanning the hole began to melt and sag. At this point the vacuum pump was tuned on (−600 mm Hg) and the foam was brought into contact with the polymer, rapidly drawing the melted polymer into the pores of the foam.

Characterization

Figure 7A:
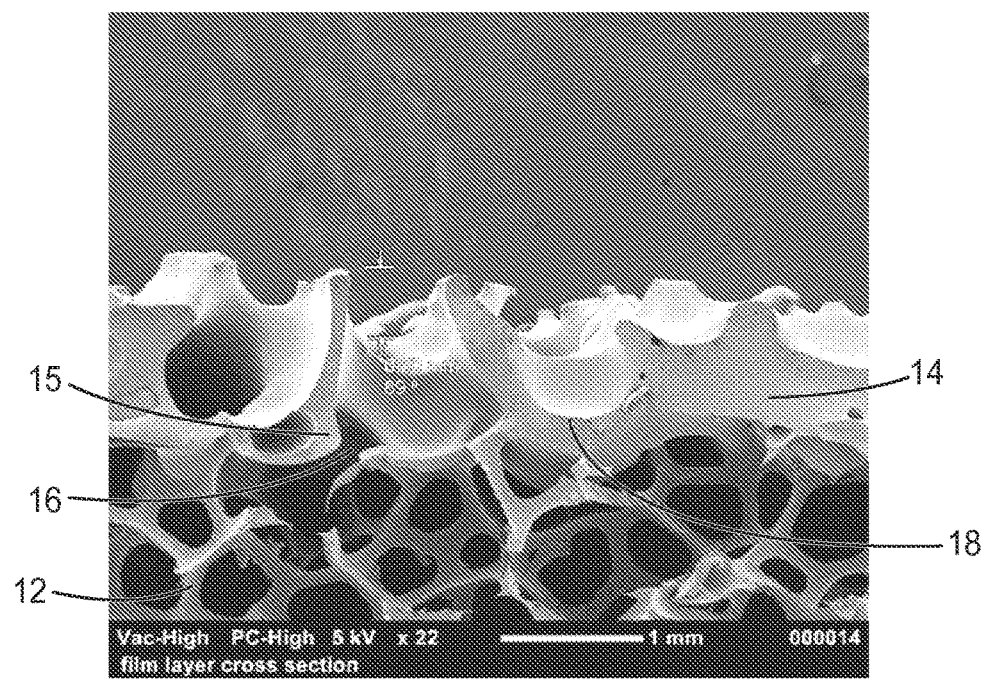
FIG. 7A is an SEM image of a cross-section of an exemplary article.
Figure 7B:
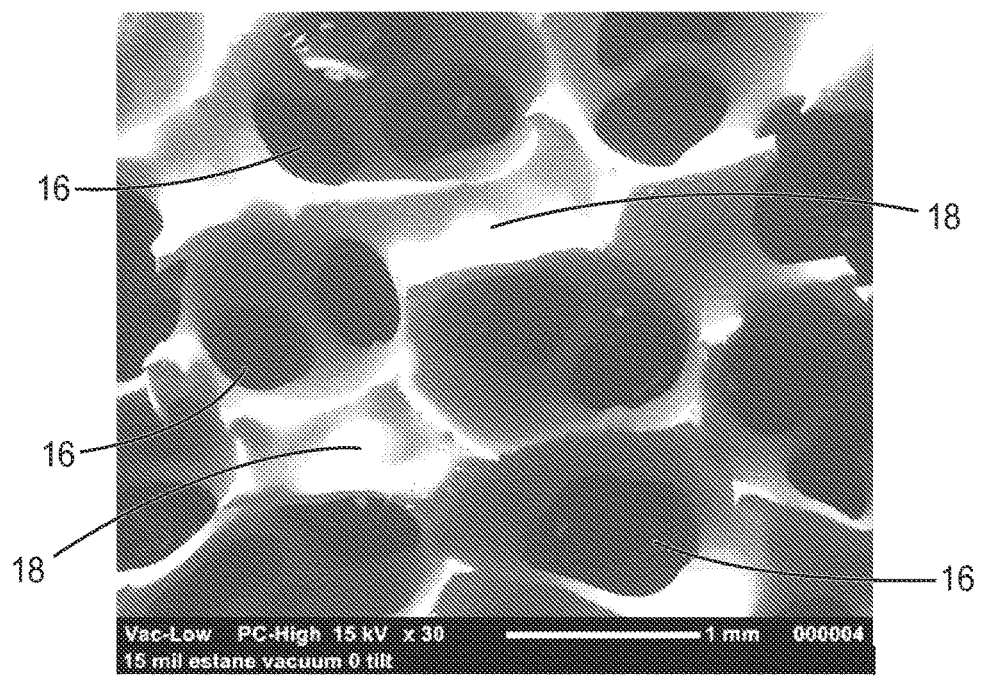
FIG. 7B is an SEM image of the top of the exemplary article of FIG. 7A.

After vacuum forming the foam layer was characterized using scanning electron microscopy (SEM). Gold was sputtered on to the sample prior to imaging (Denton Vacuum, 90 seconds). Cross sections were obtained by sectioning the samples in the Z axis using a razor blade, cutting from the foam side towards the elastomeric film side. FIG. 7A shows the SEM including the porous elastomeric material 12 and the elastomeric material 14 integrated into the first major surface of the porous elastomeric material. The polymer layer was observed to be approximately 1.5 mm thick with thin, elongated walls extending downward from the outermost struts with periodic openings in the polymer layer. One area each of the first portion of the elastomeric material 15 and of the second portion of the elastomeric material 18 is indicated on the SEM. When observed from directly overhead (FIG. 7B) approximately 50% of the foam pores 16 were observed to have corresponding openings in the polymer proximal to the vacuum source with the others pores bridged by an intact polymer layer (e.g., the second portion of the elastomeric material 18).

Deformation of skin substitute under vacuum and simulation of ingrowth

Figure 8:
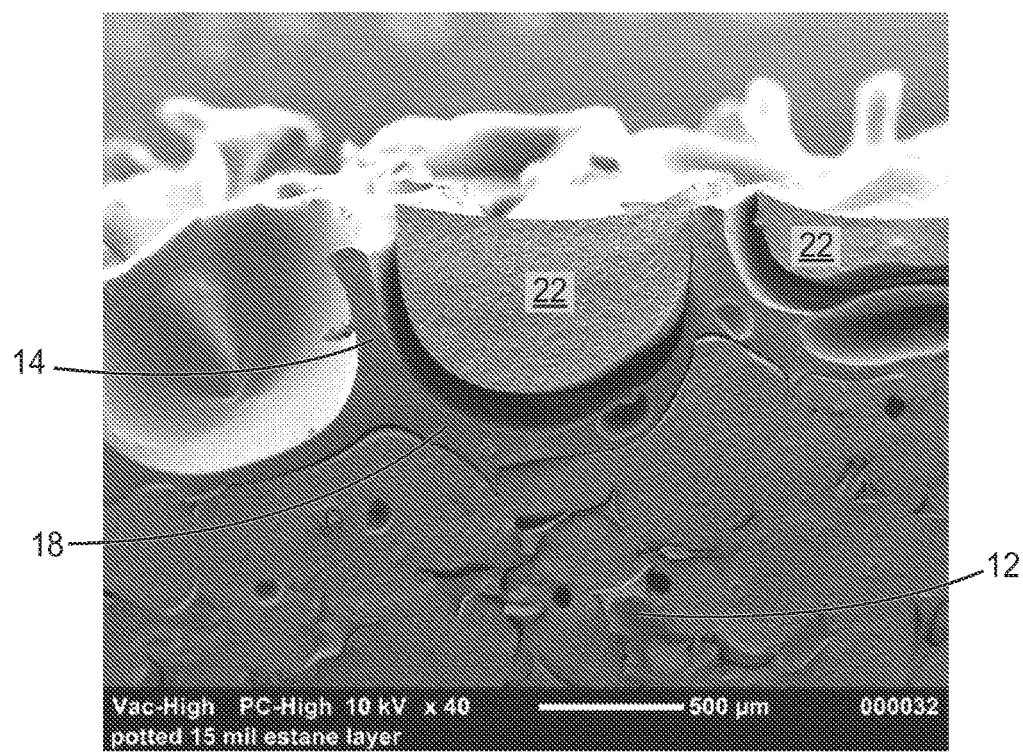
FIG. 8 is an SEM image of a cross-section of an impression material and an exemplary article of the simulation of ingrowth example.

The deformation of a skin substitute material and simulation of ingrowth was assessed simultaneously using the following procedure. The bottom 2.54 cm of a 100 ml plastic beaker was removed using a hack saw. A hole was created in one side to which a threaded female Leur lock adapter was inserted, using two rubber O rings to ensure a vacuum tight seal to the plastic. A 35 mm diameter by 10 mm tall section of DERMASOL DS-300 skin substitute (California Medical Innovations) was placed in the container. A sample of foam (Black Granufoam, KCI) 25 mm diameter by 10 mm tall was placed on the top surface of the DERMASOL. A 200 microliter pipette tip (Eppendorf) was then inserted between the foam and DERMASOL, approximately 1 cm from the edge of the foam. A 10.2×10.2 cm section of TEGADERM film was removed from 3M TEGADERM Transparent Film Roll 16004 (3M Company, St. Paul, Minn.), draped over the stack, taking care to wrap the pipette tip to ensure a vacuum seal. The tip from Imprint™ 3 VPS Impression Material (yellow, medium set, available from 3M ESPE of St. Paul, Minn.) was placed inside the pipette tip after fully filling the tip with the dental impression material and secured using electrical tape. A hose connected to a vacuum pump was inserted in to the luer lock. The pump was set to −125 mm Hg and the system evacuated, compressing the foam against the DERMASOL. The impression material was slowly introduced at the foam/DERMASOL interface while the system was under vacuum. After addition the impression material was allowed to set for 5 minutes, at which time the vacuum was turned off and the TEGADERM removed. The foam/cured impression material was removed from the DERMASOL. The material was sectioned and imaged as described above for samples generated from untreated foam and foam containing the elastic, porous film layer. SEM cross-sections showed that the material flowed across the DERMASOL interface and migrated through the pores in the elastomeric layer into the foam. Cross-section images indicated that the impression material was blocked from migrating parallel to the first major surface. The foam only control sample showed foam embedded in the impression material. In particular, FIG. 8 is an SEM illustrating a cross-section of the article including the elastomeric material 14 integrated into the first surface of the porous elastomeric material 12, and impression material 22 blocked from contacting the porous elastomeric material 12 by a second portion of the elastomeric material 18.

Figure 9:
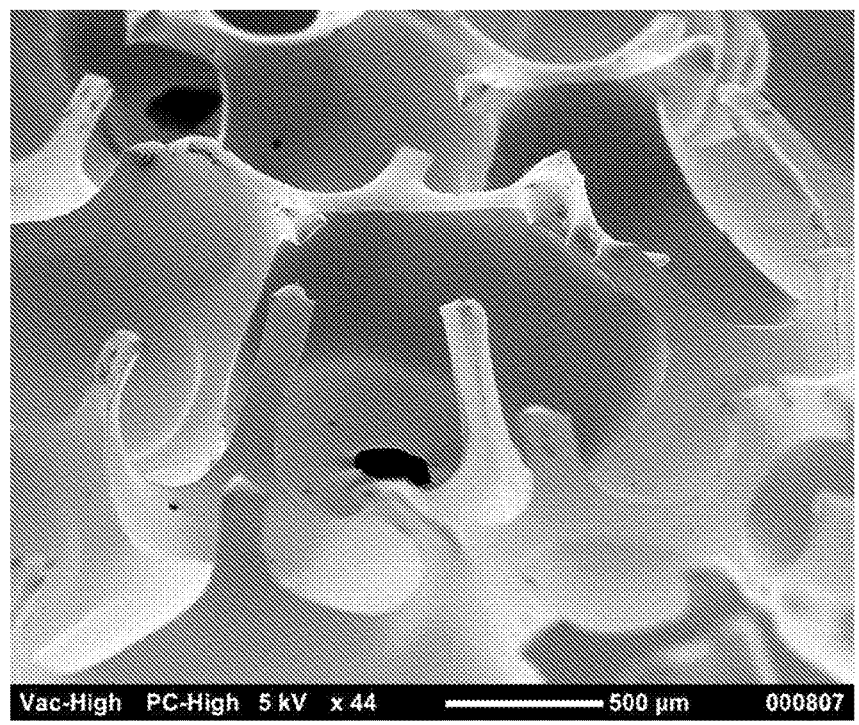
FIG. 9 is an SEM image of the top of an exemplary article.

Latex Example:

Reticulated polyether polyurethane foam (Crest Foam Industries, Inc., Moonachie, N.J., product code BC45MXA00) having having an average number of lineal pores per inch of 45 (PPI), which is equivalent to 114 pores per lineal centimeter, and a density of 20.8-25.6 Kg/cubic meter (1.3-1.6 lbs/cubic foot) was cut into a dimension of 5 cm×5 cm×1 cm. An air knife was fabricated from two 6 cm×6 cm sheets of 225 micron thick polypropylene adhered together along two edges using 1 cm wide 150 micron thick double coated tape (9425HT, 3M Company). The gap on one end of the air knife was affixed to 0.635 cm (¼ inch) TYGON tubing via a round-to-flat adapter and sealed using electrical tape. The tubing was affixed to a pressurized nitrogen source. Approximately 0.5 milliliter of TufCOR™ 1214 polyvinyl alcohol stabilized vinylacetate/ethylene copolymer (Celanese Emulsion Polymers, Dallas, Tex.) was dispensed in a line using a transfer pipette on to the top surface of the foam approximately 1 cm from an edge, generating a bead of solution approximately 3 cm long and 0.5 cm wide. The nitrogen source was adjusted to a flow volume of approximately 30 liters per minute. The air knife was then brought into contact with the surface of the foam parallel to the bead of solution. The knife was then moved laterally over the surface of the foam at approximately 0.5 cm per second through the polymer solution to spread it laterally across the surface. During coating the nitrogen stream from the air knife caused the polymer solution to penetrate below the top surface of the foam and also generate periodic openings (pores) in the coating. After the coating step film formation was allowed to proceed via air drying for 24 hours at room temperature. The resulting coated layer was characterized using SEM as described above, a top view of which is shown in FIG. 9. The polymer layer penetrated in to the foam approximately 0.8 mm with thin, elongated walls extending downward from the outmost struts in the foam with periodic openings generated by the nitrogen stream. Approximately 20% of the original foam pores were observed to have corresponding openings in the elastomeric polymer layer.

While the specification has described in detail certain exemplary embodiments, it will be appreciated that those skilled in the art, upon attaining an understanding of the foregoing, may readily conceive of alterations to, variations of, and equivalents to these embodiments. Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. An article comprising:
   a porous elastomeric material comprising a first major surface; and
   an elastomeric material integrated into the first major surface of the porous elastomeric material, wherein the porous elastomeric material comprises an average pore size of 400 μm to 700 μm, the elastomeric material coating the first major surface, a first portion of the elastomeric material being disposed within a plurality of pores defined by the first major surface of the porous elastomeric material and extending into the plurality of pores to a depth of at least 300 μm, wherein the first portion of the elastomeric material comprises an average pore size of 300 μm to 700 μm, wherein the first portion of the elastomeric material disposed within the plurality of pores blocks communication through the porous elastomeric material in a direction parallel to the first major surface, wherein the first portion of the elastomeric material provides fluid communication through the porous elastomeric material via holes formed in the elastomeric material and extending into the thickness of the porous elastomeric material through the voids of the pores of the porous elastomeric material, a second portion of the elastomeric material being disposed within a plurality of pores defined by the first major surface of the porous elastomeric material and extending into the plurality of pores to an average depth of less than 300 μm, wherein the second portion of the elastomeric material blocks the plurality of pores and block communication into the porous elastomeric material in a direction normal to the first major surface.

2. The article of claim 1 wherein the first portion of the elastomeric material disposed within the plurality of pores extends to a depth of between 300 μm and 1000 μm.

3. The article of claim 1 wherein the first portion of the elastomeric material comprises a wall thickness that decreases as the depth into the porous elastomeric material increases.

4. The article of claim 1 wherein communication through the porous elastomeric material in a direction parallel to the first major surface is blocked between a depth of 50 μm and 1000 μm into the porous elastomeric material.

5. The article of claim 1 wherein the porous elastomeric material comprises an open cell foam.

6. The article of claim 1 wherein the porous elastomeric material comprises polyurethane.

7. The article of claim 1 wherein the elastomeric material comprises polyurethane, poly(vinyl alcohol), or a polyurethane copolymer.

8. The article of claim 1 wherein the porous elastomeric material and the elastomeric material integrated into the first major surface of the porous elastomeric material comprises latex.

9. A method of making an article comprising:
providing a porous elastomeric material comprising a first major surface;
providing an elastomeric material;
contacting the elastomeric material with the first major surface of the porous elastomeric material; and
applying force to the elastomeric material thereby coating the first major surface and drawing a first portion of the elastomeric material into a plurality of pores defined by the first major surface of the porous elastomeric material and extending into the plurality of pores to a depth of at least 300 μm and forming a second portion of the elastomeric material being disposed within a plurality of pores defined by the first major surface of the porous elastomeric material and extending into the plurality of pores to an average depth of less than 300 μm,
wherein the elastomeric material is integrated into the first major surface of the porous elastomeric material, wherein the porous elastomeric material comprises an average pore size of 400 μm to 700 μm,
wherein the first portion of the elastomeric material provides fluid communication through the porous elastomeric material via holes formed in the elastomeric material and extending into the thickness of the porous elastomeric material through the voids of the pores of the porous elastomeric material, wherein the first portion of the elastomeric material disposed within the plurality of pores blocks communication through the porous elastomeric material in a direction parallel to the first major surface, wherein the first portion of the elastomeric material comprises an average pore size of 300 μm to 700 μm, wherein the second portion of the elastomeric material blocks the plurality of pores and block communication into the porous elastomeric material in a direction normal to the first major surface.

10. The method of claim 9 wherein the force is positive pressure and the elastomeric material is located between the porous elastomeric material and a source of the positive pressure.

11. The method of claim 9 wherein the force is provided by a flow of air, nitrogen, argon, or a combination thereof.

12. The method of claim 9 wherein the force is vacuum and the porous elastomeric material is located between the elastomeric material and a source of the vacuum.

13. The method of claim 9 wherein the force is gravity.

14. The method of claim 9 wherein the providing the elastomeric material comprises providing a film having a thickness between 5 μm and 20 μm.

15. The method of claim 9 wherein the providing the elastomeric material comprises providing a melted film, and the contacting the elastomeric material comprises casting the melted film on the first major surface of the porous elastomeric material.

16. The method of claim 9 wherein the providing the elastomeric material comprises providing a water-soluble emulsion comprising a solvent and an elastomeric material dispersed in the solvent or providing a solution comprising an elastomeric material dissolved in an organic solvent.

* * * * *